United States Patent [19]

Fahnestock et al.

[11] 3,991,882

[45] Nov. 16, 1976

[54] METHOD AND APPARATUS FOR INSPECTING ARTICLES FOR OPENINGS

[75] Inventors: Melvin R. Fahnestock; Kirby I. Thornton, both of Apollo, Pa.

[73] Assignee: Aluminum Company of America, Pittsburgh, Pa.

[22] Filed: May 30, 1975

[21] Appl. No.: 582,226

[52] U.S. Cl. .......................... 209/73; 209/111.7 T; 250/223 B; 356/237
[51] Int. Cl.² ......................................... B07C 5/344
[58] Field of Search ......... 209/73, 111.7, 74, 111.5, 209/111.8; 250/223 R, 223 B, 237 R, 572; 356/237

[56] References Cited
UNITED STATES PATENTS

| | | | |
|---|---|---|---|
| 2,321,331 | 6/1943 | Sweezey | 209/111.7 UX |
| 3,416,659 | 12/1968 | Linderman et al. | 209/111.7 |
| 3,826,923 | 7/1974 | Trimble | 250/572 |

*Primary Examiner*—Allen N. Knowles
*Attorney, Agent, or Firm*—David W. Brownlee

[57] ABSTRACT

An apparatus and method are disclosed for inspecting a series of can ends as they come off a forming press wherein the can ends are carried on a continuous belt which moves them through the forming press and then past a light source and a light detecting means which senses any light passing through each of the can ends as they are presented seriatim to the light source and sensing means. The light source is fixedly positioned on one side of the continuous belt and the sensing means is fixedly positioned on the other side of the belt. An extensible bellows, sealed against the light sensing means, is connected to a ram on the forming press which extends and contracts the bellows into and out of light tight sealing engagement with each of the can ends as it is presented for inspection. The light source and the light sensing means are both activated when the bellows is in light tight engagement against a can end to expose one side of the can end to light and sense whether any light passes through such can end.

9 Claims, 3 Drawing Figures

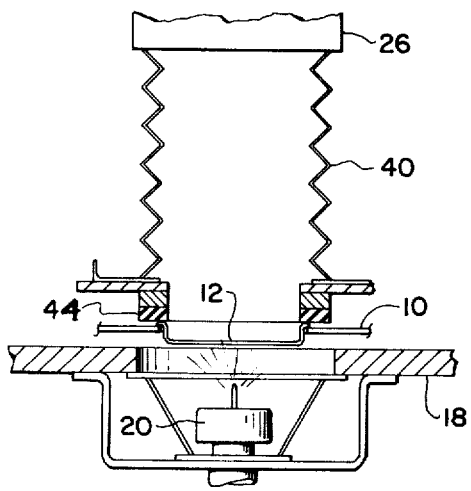
Fig. 3
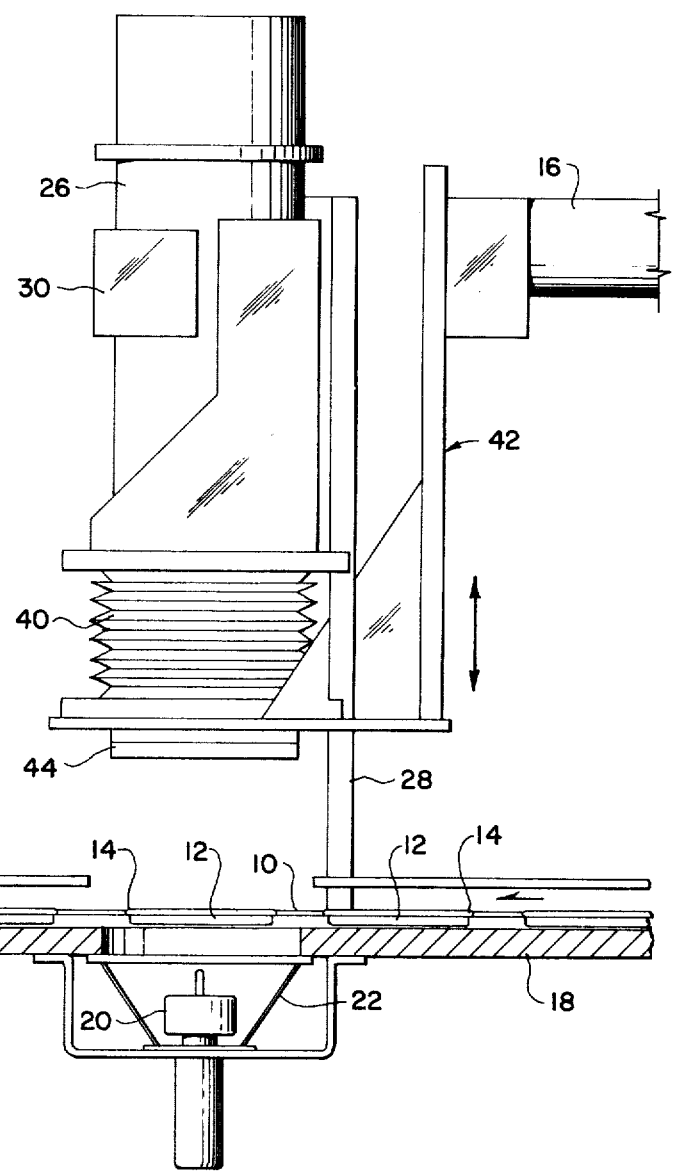
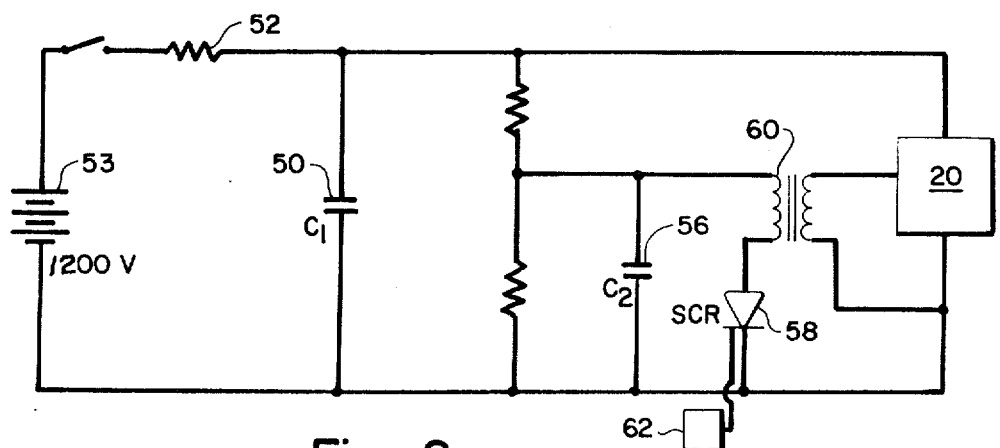
Fig. 1
Fig. 2

3,991,882

METHOD AND APPARATUS FOR INSPECTING ARTICLES FOR OPENINGS

BACKGROUND OF THE INVENTION

1. Field of Art

This invention relates to inspection means and in particular to a method and apparatus for determining whether light or other radiation will pass through an article such as a can end which is inspected for small openings.

2. Description of the Prior Art

It is well known to inspect for holes in articles by shining a light on one side of the article and inspecting the opposite side for light emanating from openings in the article using photosensitive means such as a photoelectric cell or the like. Systems of that type are disclosed in a number of U.S. Pat. Nos. such as Linderman et al 3,416,659; Phillips 3,453,054; Dvacho et al 3,750,877 and Trimble et al 3,826,923 among others.

In employing light to inspect articles, the light sensitive or photosensitive means must usually be shielded against ambient light and against light from the source passing around the article which is being inspected. A common way of shielding the photosensitive means is to put it in a light tight enclosure having an aperture or apertures therein in which the articles to be inspected are positioned during inspection. The use of such a light tight enclosure can slow the inspection process and can present problems in locating the photosensitive means in close quarters such as adjacent a press on which the articles are being formed. The photosensitive means is also usually relatively sensitive to vibrations and impact which could damage such means. It is therefore desirable for the photosensitive means to be disposed in a fixed position and insulated from shock.

An improved method and apparatus are desired for rapidly inspecting opaque articles for openings therethrough.

SUMMARY OF THE INVENTION

An apparatus and method are provided for inspecting a series of opaque articles for openings therethrough by presenting the articles seriatim between means for producing optical radiation and means for sensing such radiation having an extensible conduit on it which is extended into light tight engagement with each article as it is presented for inspection. The extensible conduit may comprise a light tight welded metal diaphragm bellows having a compressible sealing ring on its end for producing a light tight seal against the article to be inspected around the area to be inspected. The bellows may be connected to a movable ram on a press for forming the articles to be inspected to extend and contract the bellows as each article is presented seriatim for inspection. The radiation producing means and radiation sensing means are activated after the light tight engagement has been made and deactivated before such engagement is broken.

Accordingly, an object of this invention is to provide an improved method and apparatus for rapidly inspecting articles for small openings therethrough.

Another object of this invention is to inspect articles for openings therethrough by presenting them seriatim between optical radiation producing means and optical radiation sensing means, producing light tight engagement between the article and the radiation sensing means, and activating the radiation producing means and radiation sensing means to expose one side of the article to radiation and sense whether any of the radiation passes through the article.

A further object of this invention is to provide an extensible welded metal diaphragm bellows which acts as a light tight conduit between a light sensing means and an article to be inspected. The bellows may be connected to the movable ram on a press for forming the article to extend and retract the bellows to produce light tight engagement with each article as it is presented for inspection.

A further object of this invention is to provide a system for inspecting articles for small openings therethrough in which the articles are conveyed on a continuous belt which moves the articles seriatim into position for inspection between the radiation producing means and a radiation sensing means to inspect the articles for opening and then moves the articles to a means for ejecting any defective articles from the continuous belt.

Other objects and advantages of this invention will be more fully understood and appreciated with reference to the following description and the drawings appended hereto.

BRIEF DESCRIPTION OF THE DRAWINGS

FIG. 1 shows a side elevation of apparatus of this invention.

FIG. 2 is a schematic illustration of the controls for this invention.

FIG. 3 is a fragmentary cross-sectional view of the apparatus of FIG. 1 showing a can end as it is being inspected.

DESCRIPTION OF PREFERRED EMBODIMENTS

A preferred embodiment of a system of this invention for inspecting articles for small openings therein is generally illustrated in FIGS. 1 and 2. The system generally comprises a continuous belt 10 having spaced openings therein for receiving and carrying articles such as can ends 12 to be inspected. Can ends 12 typically include a central panel portion and a peripheral flange 14 therearound which is adapted to be double seamed onto a container such as a can body. The openings in the continuous belt 10 are dimensioned to receive the central panel portion of a can end with the peripheral flange 14 seated on the belt around the opening therein. Belts of this type are in use in conveying end blanks or end shells through forming presses for converting the end shells into easy opening ends with severable opening panels therein. The apparatus of this invention is adapted to be mounted on or adjacent to such a conversion press for inspecting the can end immediately after they have been converted into easy opening ends. The numeral 16 is used to generally designate the movable ram on a press which is adapted to convert end shells into easy opening ends. The numeral 18 is used to generally designate the table on the press over which the end shells and converted ends are moved.

The travel of the belt 10 in conveying the end shells and converted easy opening ends 12 through the conversion press is intermittent. In other words, the end shells are presented seriatim to a location between the dies in the conversion press and stopped in such location as the dies are moved together to convert the end shell into an easy opening end. There may be multiple operations in such conversion with the end shells being moved intermittently between each operation. FIG. 1 shows the belt 10 and converted easy opening ends 12 as they come from the forming dies in such a conversion press.

In accordance with this invention, an optical radiation producing means such as a xenon strobe light 20 is mounted on the table 18 on the conversion press in a fixed position below the table. The strobe light is preferably mounted on the press by means of a vibration dampening or vibration free mounting means to insulate the strobe light from shock and vibrations in the press during the conversion of end shells into easy opening ends. The table 18 has a hole therethrough above the strobe light 20 for light or other radiation to pass through the table to irradiate the undersurface of the can end positioned above the hole. The strobe light 20 is positioned in a conical reflector 22 directed upwardly toward the hole in the table so that a maximum of radiation will be directed toward the undersurface of each can end as it is presented for inspection.

A radiation sensing means such as a photodetector 26 is mounted on the conversion press in a fixed position above the table in vertical alignment with the strobe light 20 below the table. The photodetector 26 is mounted on the table 18 on the press by means of a vibration dampening mounting bracket 28 with a clamp 30 which is secured around the housing for the photodetector.

An extensible welded stainless steel bellows 40 is secured on the end of the photodetector 26 for providing a light tight conduit between the photodetector and each can end 12 as it is presented for inspection. The lower end of the bellows 40 is connected to the movable ram 16 on the conversion press through an L-shaped connector arm 42. When the movable ram is moved vertically during the conversion of end shells into easy opening ends, the movement of such ram extends and contracts the bellows 40.

The lower end of the bellows 40 has a sealing ring 44 thereon for producing a light tight seal against the peripheral flange 14 on each can end when the bellows is extended toward such can end. The sealing ring 44 may comprise a compressible plastic material which is opaque against transmission of radiation to prevent any light or other radiation from passing between the bottom end of the bellows and the peripheral flange on a can end.

FIG. 1 further illustrates means for rejecting defective can ends from being carried by the belt 10. The table 18 has an aperture therethrough with a high pressure air line 46 connected thereto and an air nozzle 48 seated in the aperture to produce an air jet which will blow a can end 12 out of the hole in the belt 10 in which such can end is carried. A chute 38 is mounted on the press above the ejection means to carry the ejected can ends safely from the press into a waste container which may be positioned adjacent thereto. To assist the air jet, a small pin or the like, not shown, may be mounted on the table 18 to engage the undersurface of each can end and help free it from its seating in the belt and thereby insure that the air jet from nozzle 48 will eject the can end from the belt.

If the can ends which have been inspected are found to have no small openings therethrough, the air jet is not employed. Instead, the can ends continue with the belt to a later station at which the can ends are removed from the belt and stacked or transferred to a further operation.

In accordance with this invention, an electronic eye is provided which is actuated by the bottom end of the bellows 40 or the arm 42 carrying such bellows to activate the strobe light 20 and the photodetector 26 when the bellows is in the extended condition and the sealing ring is in light tight engagement against the peripheral flange on a can end. The controls are so programmed that the light source and photodetector are activated for only a very short duration, such as approximately 100 microseconds, which is considerably less than the period during which the sealing ring 44 is sealed against the peripheral chine on a can end. Consequently, during the period in which the photodetector is activated, the only light which can reach the photodetector is light passing through any opening in the can end which is being inspected. At all other times, the photodetector is inactive, and any light reaching such photodetector will not be recorded nor produce a resultant defect signal.

FIG. 2 is a schematic of the power supply and controls for apparatus of this invention. The strobe light 20 may be fired by a capacitive discharge device wherein a capacitor 50 is charged through a resistor 52 from a power source such as a battery 53 or a source of rectified AC current. A second capacitor 56 is also charged to a lower voltage by the same source. A switching device such as a silicon-controlled-rectifier (SCR) 58 in series with the primary winding of a transformer 60 is placed across capacitor 56. The secondary winding of transformer 60 is connected to the radiation source. A trigger signal from the photoelectric cell 62 is applied to the gate of the SCR 58 biasing the SCR into conduction to thus discharge capacitor 56. The flow of current from the capacitor 56 through the primary winding of the transformer 60 causes the secondary winding to deliver a high voltage pulse to the radiation source. The radiation source in a preferred embodiment of this invention comprises a gas-filled ionizable source, such as, for example, a xenon gas-filled source. The pulse from transformer 60 ionizes the xenon gas thus causing changing its resistance and causing capacitor 50 to discharge. The radiation or light which is produced by such discharge irradiates the undersurface of the can end 12 which is positioned over the strobe light 20. If the can end has any small openings in it, the high intensity radiation will pass through such small openings and will be detected by the photodetector 26. The photodetector 26 will produce a signal to the control system that the can end which has been inspected has small openings in it and should be rejected.

In the apparatus selected for illustration, the reject means is located two stations or two can ends away from the can end which is inspected. The controls are therefore programmed to produce a jet of air at such reject station two cycles after the defective end has been inspected. When the defective end stops at the reject station two cycles later, a jet of air will blow the defective end from the continuous belt 10, through chute 38 and into a waste container.

The operation of apparatus of this invention is extremely high speed such as approximately 300 or more cycles per minute. Each time the conversion press is cycled to complete the conversion of an end shell into an easy opening end, the movable ram on such press also extends the bellows of this invention to produce a light tight seal with a can end to be inspected and activates the light source and photodetector to inspect a can end positioned therebetween. Since the photodetector need not be enclosed in a completely light tight enclosure as with most prior art devices, the apparatus of this invention is adapted to be mounted on the table of a conversion press and is operated simultaneously therewith. The device is effective in inspecting for very small openings in can ends or other similar articles and inspects 100 percent of the articles coming off the conversion press.

The extensible conduit which is used in this apparatus is preferably a welded diaphragm metal bellows which is opaque to light and which can be cycled at a very high rate for an almost infinite number of cycles without failure. Bellows of this type are available from a number of sources such as Metal Bellows Company of Sharon, Massachusetts. As an alternative to such metal bellows, a telescoping tube may be employed in this invention so long as such tube provides a conduit through which radiation may pass from the article being inspected to the photodetector without permitting any ambient or extraneous light to reach the photodetector. Although this invention has been illustrated and described in terms of a particular embodiment, this invention is understood to include all variations of such embodiment within the scope of the claims appended hereto.

What is claimed is:

1. Apparatus for inspecting a series of opaque articles for openings therethrough comprising:

stationary means for producing optical radiation;
   stationary means for detecting optical radiation;
   conveying means for presenting articles seriatim in a predetermined position between said radiation producing means and said radiation detecting means;
   an extensible opaque conduit with one end thereof secured on said radiation detecting means and the other end having a sealing means thereon for producing light tight engagement against an article around the area thereof to be inspected for openings;
   means for extending said conduit to engage said sealing means in light tight engagement against each article as it is presented for inspection, and for contracting said conduit after inspection of the article; and
   means for activating said detecting means upon achieving said light tight engagement of said conduit against each article and for inactivating the detecting means prior to breaking said light tight engagement.

2. Apparatus as set forth in claim 1 in which said extensible conduit comprises light tight diaphragm metal bellows having a compressible sealing ring on the end thereof for producing a light tight seal against each article to be inspected.

3. Apparatus as set forth in claim 1 which is disposed adjacent a press for forming the articles to be inspected and a movable ram on the press is connected to said conduit to extend and contact same.

4. Apparatus as set forth in claim 1 which includes means for storing energy for said radiation producing means and for activating said radiation producing means to release stored energy in a short burst of radiation when light tight engagement is made between said conduit and the article to be inspected and deactivate both means before such engagement is broken.

5. Apparatus as set forth in claim 1 which includes means for ejecting from said conveying means articles found to have holes therein.

6. Apparatus as set forth in claim 5 in which said ejection means comprises an air jet.

7. Apparatus as set forth in claim 1 in which said conveying means comprises a continuous opaque belt with holes therein for receiving articles to be inspected.

8. A method of inspecting a series of opaque articles for openings therethrough comprising the steps of:

presenting articles seriatim to an inspection location between a stationary means for producing optical radiation and a stationary means for detecting optical radiation having an extensive opaque conduit secured thereon;
   extending the opaque conduit toward each article as it is presented for inspection into light tight engagement against each article; and
   activating the radiation producing means and the radiation sensing means when the conduit is in light tight engagement with an article to be inspected to irradiate one surface of the article and sense any radiation passing through such article.

9. A method as set forth in claim 8 in which articles found to have openings therein are ejected from the conveying means subsequent to inspection.

* * * * *